(12) United States Patent
Houben et al.

(10) Patent No.: US 6,605,039 B2
(45) Date of Patent: Aug. 12, 2003

(54) CELL-BASED BIOSENSORS SUITABLE FOR IMPLANTABLE MEDICAL DEVICE APPLICATIONS

(75) Inventors: Richard Houben, Lanaken (BE); Vincent Larik, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/909,999

(22) Filed: Jul. 23, 2001

(65) Prior Publication Data

US 2002/0038083 A1 Mar. 28, 2002

Related U.S. Application Data

(60) Provisional application No. 60/220,773, filed on Jul. 24, 2000, and provisional application No. 60/220,774, filed on Jul. 24, 2000.

(51) Int. Cl.$^7$ .............................. A61B 5/00; A61B 5/05
(52) U.S. Cl. ...................................... 600/365; 600/347
(58) Field of Search ............................... 600/365, 345, 600/347, 366, 372, 309, 300

(56) References Cited

U.S. PATENT DOCUMENTS

| | | | |
|---|---|---|---|
| 5,050,612 A | | 9/1991 | Matsumura |
| 5,101,814 A | | 4/1992 | Palti |
| 5,368,028 A | * | 11/1994 | Palti ........................... 600/345 |
| 5,719,324 A | | 2/1998 | Thundat et al. |
| 5,813,763 A | | 9/1998 | Plotnikov et al. |

OTHER PUBLICATIONS

Barnes et al. A femtojoule calorimeter using micromechanical sensor. Rev. Sci. Instrum. vol. 65 (12).

Chen et al. Adsorption–induced surface stress and its effects on resonance frequency of microcantilevers. J. appl. Phys. vol. 77 (8).

Gylfe E, et al. the Heat Production of pancreatic beta–cells stimulatined by glucose. Acta physiol. Scan. OI. 93 179–183.

Verhaegen et al. A Biomedical Microphysiometer Based on Calorimetry. IMEC—Leuven, KUL Dept. of Physiology and KUL—ESAT.

* cited by examiner

*Primary Examiner*—Max F. Hindenburg
*Assistant Examiner*—Navin Natnithithadha
(74) *Attorney, Agent, or Firm*—Thomas F. Woods; Eric D. Waldkoetter; Tom G. Berry

(57) ABSTRACT

A sensing methodology is used based on measuring a physical response from a living structure as a result of a chemical compound stimulating this structure on the cellular level. Measurement of the heat response (calorimetry) from a group of pancreatic islets of Langerhans stimulated by glucose is proposed as a glucose biosensor. A novel biosensor concept is proposed acquiring physical response from living cells or cell clusters. In this particular case, membrane impedance of pancreatic B-cells, as a result of glucose stimulated cellular metabolism is used as physical readout. This method of physical assessment is made possible by growing genetically engineered pancreatic beta cells onto a substrate equipped with a set of interdigitated electrodes (IDEs).

2 Claims, 3 Drawing Sheets

CELL-BASED BIOSENSORS SUITABLE FOR IMPLANTABLE MEDICAL DEVICE APPLICATIONS

RELATED APPLICATIONS

This patent application claims priority and other benefits from U.S. Provisional Application Ser. No. 60/220,773 entitled "Cell-Based Biosensor Platform Based on Impedimetric Sensing of Cellular Activity" to Houben et al. filed Jul. 24, 2000, and incorporates the entirety of same by reference herein. This patent application also claims priority and other benefits from U.S. Provisional Patent Application Ser. No. 60/220,774 entitled "Biosensor Based on Micro-Calrimetric Detection of Pancreatic Beta Cell Activity" to Houben et al. filed Jul. 24, 2000, and incorporates the entirety of same by reference herein.

FIELD OF THE INVENTION

This invention is generally directed to the field of cell-based biosensors suitable for implantable medical device applications.

DETAILED DESCRIPTION OF THE INVENTION

Although specific embodiments of the invention are described here in some detail, it is to be understood that those specific embodiments are presented for the purpose of illustration, and are not to be taken as somehow limiting the scope of the invention defined in the appended claims to those specific embodiments. It is also to be understood that various alterations, substitutions, and modifications may be made to the particular embodiments of the present invention described herein without departing from the spirit and scope of the appended claims.

All printed publications, patents and patent applications referenced hereinabove, hereinbelow, in U.S. Provisional Patent Application Ser. No. 60/220,773 entitled "Cell-Based Biosensor Platform Based on Impedimetric Sensing of Cellular Activity" to Houben et al. filed Jul. 24, 2000, and in U.S. Provisional Application Ser. No. 60/220,774 entitled "Biosensor Based on Micro-Calrimetric Detection of Pancreatic Beta Cell Activity" to Houben et al. filed Jul. 24, 2000, are hereby incorporated by reference herein, each in its respective entirety.

Figure 1:
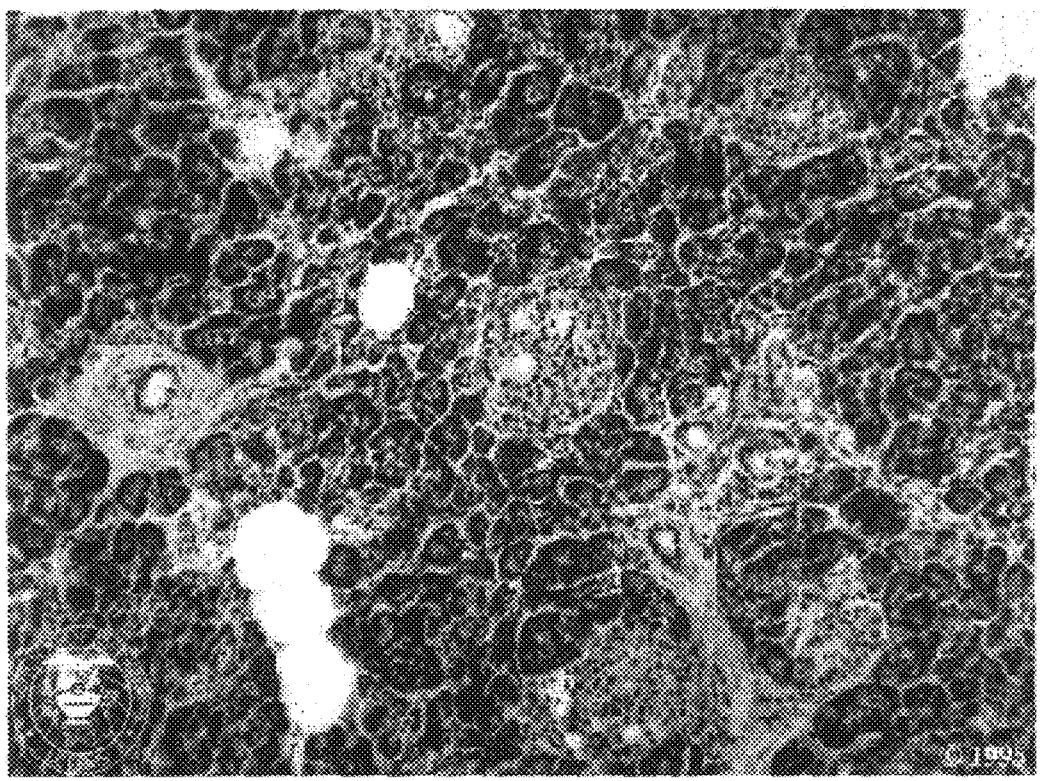
FIG. 1 shows pancreatic islets of Langerhans.

Encapsulated (rodent) pancreatic islets exposed to, either interstitial body fluids of in direct contact with streaming blood, provide the basis for the proposed biosensor. Glucose will duffuse through the semipermeable membrane and through the cellular membrane of pancreatic beta cells, which gives rise to formation of adenosine triphosphate (ATP), as illustrated in FIG. 1. ATP must be seen as the main cellular energy carrier fueling cellular processes of general importance like the sodium potassium pump maintaining the membrane potential, but also very specific functions like the release of intracellular insulin granules. Formation of ATP (enzymatically controlled by F1-ATPase) does not produce heat, however utilization of ATP fueling the various cellulalr functions does. For pancreatic islets, 50 nW/islet is produced in basal state (5.5 mM glucose), increasing towards 90 nW/islet under high glucose conditions (20 mM) (Gylfe, 1974). In good non-diabetics, a rise of glucose level from basal to high takes takes place in 30 min after food intake returning back to basal levels after 90 min, while the cellular heat response as a result of glucose stimulus takes place in less then 10 minutes. The associated heat profile can be interpreted as a physical indicator of related to blood glucose concentration. A biomedical microcalimeter based on a micromachined silicon thermopile has been described recently. (Verhaegen). A thermopile is a set of n thermocouples connected thermally in parallel whilst connected in serial electrically increasing the thermal sensitivity towards the nWatt area required for sensing pancreatic islet heat production under glycemic control. See for example: Barnes et al. A femtojoule calorimeter using micromechanical sensor. Rev. Sci. Instrum. Vol 65 (12); Chen et al. Adsorption-induced surface stress and its effects on resonance frequency of microcantilevers. J. appl. Phys. Vol. 77 (8); Gylfe E, et al. the Heat Production of pancreatic beta-cells stimulatined by glucose. Acta physiol. Scan. O1.93 179–183; Verhaegen et al. A Biomedical Microphysiometer Based on Calorimetry. IMEC—Leuven, KUL Dept. of Physiology and LUL—ESAT; U.S. Pat. No. 5,719,324 Microcantilever sensor; Thundat et al. Lockheed Martin Energy Systems Inc. Oak Ridge, Tenn. USA; U.S. Pat. No. 5,101,814 System for Monitoring and Controlling Blood Glucose to Palti; U.S. Pat. No. 5,050,612 Device for Computer-Assisted Monitoring of the Body to Matsumura; and, U.S. Pat. No. 5,813,763 Ultrasensitive differential Microcalorimeter. Valerian et al., Microcal Inc. Northhampton, Mass., USA.

A novel biosensor concept is proposed acquiring physical response form living cells or cell clusters. In this particular case, heat production of pancreatic B-cells, as a result of glucose stimulated cellular metabolism is used as physical readout. Heat production, as a result of utilization of glucose, within pancreatic islets of Langerhans varies from 50 nW at baseline level up to 10 nW while stimulated with glucose. This range of variation does match sensitivity of novel heat measurement methods including micro cantilever beam technology or micromachined silicon thermopiles both operated in different mode. Feasibility of the proposed physiochemical sensor concept for B-cells will create potential for the creation of a more broadly defined sensor platform utilizing other cell types more specific for other chemical compounds. Novel biosensor concepts are investigated acquiring physical response from living cells or cell clusters. Initial experiments will focus on the assessment of heat production of in-situ pancreatic B-cells (pancreatic islets) by stimulation of glucose serving as a glucose biosensor. Heat production, as a result of utilization of glucose, within pancreatic islets of Langerhans varies from 50 nW at baseline level up to 100 nW while stimulated with glucose. This range of variation does match sensitivity of novel heat measurement methods including micro cantilever technology and micromachined silicon thermopiles both operated in differential mode.

An alternative method of physical assessment is explored by growing genetically engineered pancreatic beta cells onto a substrate equipped with a set of interdigitated electrodes. A glucose stimulus triggers cell depolarization (bursting) of the B-cells associated with opening and closing of ion channels as well as the exocytosis of insulin. Both opening and closing of ion channels and exocytosis of insulin will give rise to measurable capacitive changes in the cell membrane. Feasibility of either one or both of the proposed physiochemical sensor concepts for B-cells will create potential for the creation of a more broadly defined sensor platform.

As a spin-off fixation techniques explored within this project both are the cellular and islet level, these techniques may be used to aid onto to work done by Prof. Palti (Carmel Inc) in the field of electrical assessment of islet activity. Beside the islet fixation problem, exterior pancreatic islet cells (mostly glucagon producing alpha cells) may be destroyed during the handling of the islet tissue (both during isolation as well as during the placement procedure). When this happens, those cells start acting as an electrical barrier between vital beat cells in the core of the islet and recording electrodes. To solve these problems, a 3D (hillock) microelectrode approach is investigated. The advantage of this approach is that recording electrodes will be in close contact with vital beta cells located a couple cell layers beneath the islet surface. Furthermore, this electrode shape (e.g. Pt hillocks, 20 microns high, spaced 50 microns) will provide (initial) fixation of the islets. Having a hillocks arranged in a matrix, one set of electrodes may be used for electrical stimulation to provide B-cell synchrony within the islet which give rise to a more rigid and therefore more easy detectable signal by the other set of recording electrodes in the matrix. Besides that, measuring islet activity from more then one location provides an opportunity to select the best signal since it is known that individual beta cells have different firing thresholds. Pt microelectrode matrices can be manufactured on a silicon wafer base. A pre-amplification stage may be included on the same wafer in the direct proximity of the recording electrodes before running the signals through "long" wires for further processing and readout.

Sampling is done from the fingtip up to several times per day with a small lancet and a triggering device. As shown by the Diabetes Control and Complications Trial (DCCT 1993), the current treatment should be intensified in order to decrease the incidence of diabetic complications. Intensified treatment may be implemented by more tight insulin injection regimes (e.g. functional insulin treatment, Howorka 1996) or by means of an (implantable) insulin pump. Care must be taken not to interfere heavily with the patient's life-style since it has been shown that most IDDM patients cannot and will not adapt their life-styles to adhere to required insulin regimes. The negative result from DCCT was that improved plycemic control would induce more frequent excursions of hypoglycemia(either reactive or nocturnal) as well as creation of unawareness loosing the ability sensing an upcoming hypoglycemicexcursion. Both symptoms increase the risk of hypoglycemiccoma, which may lead to severe brain damage or even death.

Non-Insulin Dependent Diabetes Mellitus (NIDDM). NIDDM or Type-II Diabetes may also manifest itself with classical symptoms, but is often symptomatic. Insulin treatment is not always necessary, but given the progressive character of the disease, one may need it to attain adequate glycemic control. NIDDM often does not develop before the age of forty but thereafter its incidence goes up linear with age. Life expectancy of NIDDM patients is slightly shorter than in non-diabetic patients. NIDDM is a heterogeneous disorder, characterized by both defects in insulin secretion and impaired insulin action. In non-diabetic patients, the intake of a meal will induce a small increase of plasma glucose levels and subsequent rapid stimulation of insulin secretion. Insulin secretion takes place in two phases, first a rapid increase of insulin secretion lasting for 30s providing the first need followed by a more gradual second phase of insulin release. The ability of insulin secretion is impaired in NIDDM, showing complete absence of the first phase and flattening of the second phase of insulin release. Insulin stimulates glucose uptake in peripheral tissue merely skeletal muscle. The overall insulin secretion capacity of NIDDM patients is around 50% compared to non-diabetic individuals. In addition, NIDDM patients show decreased insulin sensitivity, which involves both peripheral and hepatic tissues. Although the degree of hyperglycaemia merely depends on the severity of peripheral insulin resistance, increased hepatic glucose output will contribute further to hyperglycaemia. When tissue glucose uptake is reduced, plasma glucose levels will increase until glucose is lost through the kidneys in the urine leading to large caloric, and weight loss. Insulin release and action can be improved but not normalized as a result of better metabolic control either by diet, hypoglycemic agents, or administration of exogenous insulin. New generations of DM type-II drugs, like Rezulin198 also re-sensitize the body to insulin.

Figure 2:
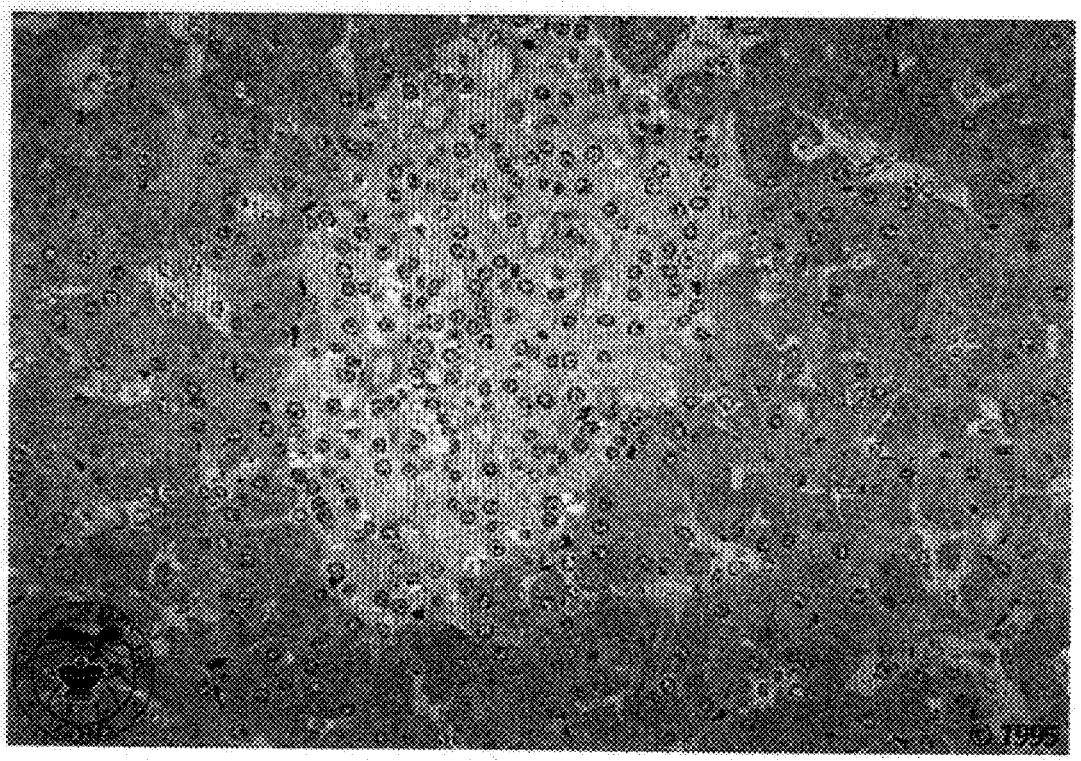
FIG. 2 shows pancreatic islets of Langerhans at higher magnification than FIG. 1.
Figure 3:
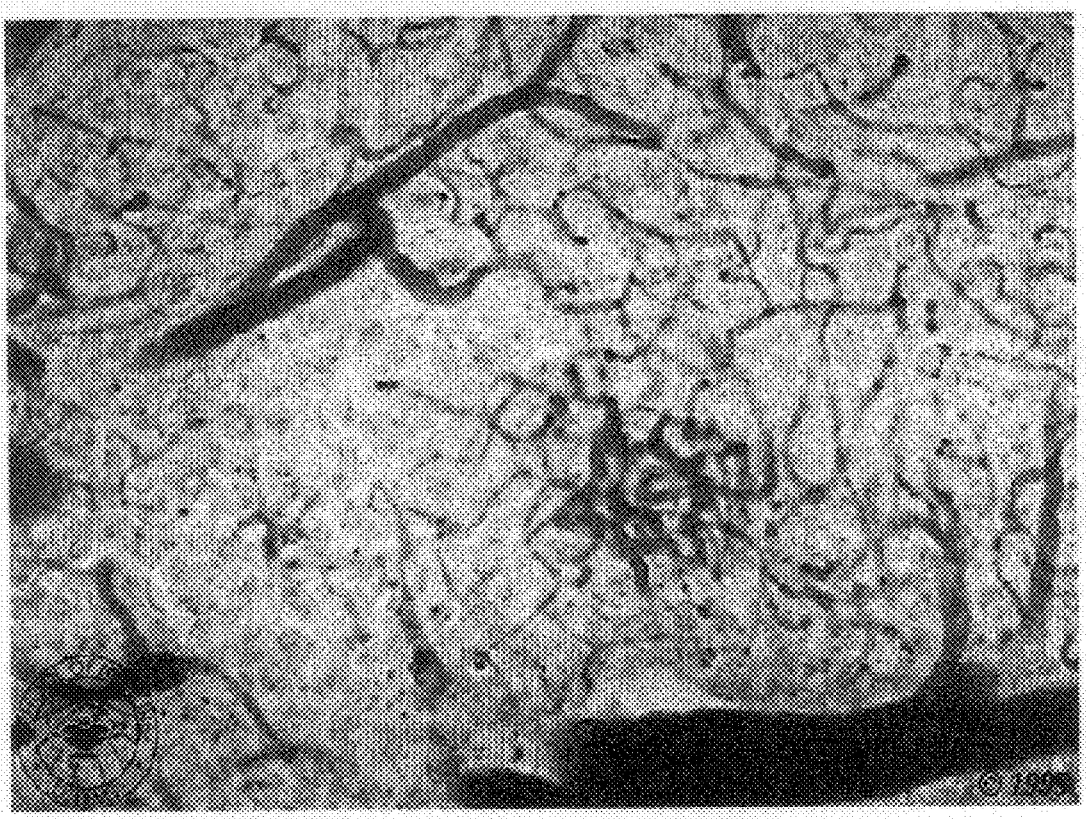
FIG. 3 shows pancreatic islets of Langerhans at higher magnification than FIG. 2.

Secondary complications are frequently observed in NIDDM patients who may have severe consequences. Complications associated with NIDDM categorize in acute metabolic effects like thirst, nonketotic coma, chronic microvascular complications like neuropathy, macroangiopathy, autonomous neuropathy, and associated conditions like hypertension (syndrome-X). In NIDDM, a two to four increase in morbidity and Harvesting of islets of Langerhans requires isolation form (rodent) pancreata by selective (enzymatic) dissociation of the exocrine pancreatic tissue while maintaining the vitality of all islets present in the pancreas (van Suijlichem), immune-isolation requires encapsulation of the islets by means of a semipermeable membrane preventing immune destruction of the sensor. See FIGS. 1, 2 and 3, where pancreatic islet of Langerhans is embedded in exocrine acinar tissue, which does comprise 99% of the pancreatic volume. The human pancreas consists of approximately 10×6 Islets ranging from less then 40 μm in diameter containing only a few cells to about 5000 cells and 400 μm in diameter containing only a few cells to about 5000 cells and 400 μm in diameter (Bonner-Weir 1994).

What is claimed is:

1. A glucose biosensor, comprising:
   a substrate having interdigitated electrodes; and,
   pancreatic beta cells grown onto the substrate, the pancreatic beta cells having cell membranes and ion channels,
   wherein when the pancreatic beta cells are exposed to insulin, the ion channels opening and closing create measurable changes in cell membrane impedance.

2. A glucose biosensor, comprising:
   a substrate having stimulation electrodes and recording electrodes, the stimulation electrodes and recording electrodes being interdigitated on the substrate; and,
   pancreatic beta cells grown onto the substrate, the pancreatic beta cells having cell membranes and ion channels, the ion channels being activated in the presence of insulin to create measurable changes in cell membrane impedance.

* * * * *